(12) United States Patent
Dressler et al.

(10) Patent No.: US 12,708,333 B2
(45) Date of Patent: Aug. 18, 2026

(54) SYSTEM AND METHOD FOR DRIVING A TRANSLATORY MOVEMENT OF A RETAINING STRUCTURE

(71) Applicant: Siemens Healthineers AG, Forchheim (DE)

(72) Inventors: Christian Dressler, Herzogenaurach (DE); Ulrich Foerner, Ebensfeld (DE); Ottmar Foerstel, Pinzberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 119 days.

(21) Appl. No.: 18/917,466

(22) Filed: Oct. 16, 2024

(65) Prior Publication Data

US 2025/0127469 A1 Apr. 24, 2025

(30) Foreign Application Priority Data

Oct. 20, 2023 (DE) ..................... 10 2023 210 368.0

(51) Int. Cl.

| | |
|---|---|
| ***A61B 6/00*** | (2024.01) |
| ***A61B 5/055*** | (2006.01) |
| ***A61B 6/03*** | (2006.01) |
| ***A61B 6/10*** | (2006.01) |
| ***A61B 6/46*** | (2024.01) |

(52) U.S. Cl.
CPC ............ *A61B 6/4405* (2013.01); *A61B 6/107* (2013.01); *A61B 6/462* (2013.01); *A61B 5/055* (2013.01); *A61B 6/03* (2013.01); *A61B 6/032* (2013.01); *A61B 6/035* (2013.01); *A61B 6/4441* (2013.01)

(58) Field of Classification Search
CPC ........ A61B 6/4405; A61B 6/107; A61B 6/462
See application file for complete search history.

(56) References Cited

U.S. PATENT DOCUMENTS

| | | | | |
|---|---|---|---|---|
| 2002/0003854 A1* | 1/2002 | Ivan | A61B 6/4441 378/20 |
| 2008/0093568 A1* | 4/2008 | Fox | G21F 1/02 250/515.1 |
| 2014/0288410 A1* | 9/2014 | Takamori | A61B 5/055 600/415 |
| 2015/0028873 A1* | 1/2015 | Dohata | G01R 33/385 324/322 |
| 2017/0325763 A1* | 11/2017 | Hoernig | A61B 6/4405 |
| 2018/0146933 A1* | 5/2018 | Lerch | A61B 6/032 |
| 2019/0090830 A1 | 3/2019 | Gao | |

* cited by examiner

*Primary Examiner* — Chih-Cheng Kao
(74) *Attorney, Agent, or Firm* — Harness, Dickey & Pierce, P.L.C.

(57) ABSTRACT

In the system, a retaining structure is configured to move relative to an examination area via a guide apparatus, and the retaining structure has a first connection unit. A gantry is configured to move relative to the examination area via a running gear, wherein the running gear is configured to drive a translatory movement of the gantry relative to the examination area. The gantry has a second connection unit, wherein the first connection unit and the second connection unit are configured to establish a connection that counteracts a change of position of the retaining structure relative to the gantry such that the retaining structure follows the translatory movement of the gantry relative to the examination area when the connection is established. The retaining structure is configured to move relative to the gantry via the guide apparatus when the connection is released.

20 Claims, 3 Drawing Sheets

MOVE THE RETAINING STRUCTURE
M1
ESTABLISH CONNECTION
M2
DRIVE TRANSLATORY MOVEMENTOF THE GANTRY
M3

SYSTEM AND METHOD FOR DRIVING A TRANSLATORY MOVEMENT OF A RETAINING STRUCTURE

CROSS-REFERENCE TO RELATED APPLICATION(S)

The present application claims priority under 35 U.S.C. § 119 to German Patent Application No. 10 2023 210 368.0, filed Oct. 20, 2023, the entire contents of which are incorporated herein by reference.

FIELD

One or more example embodiments of the present invention relate to a system with a gantry of a medical imaging device and a retaining structure for retaining a component for a medical imaging examination of an examination area. One or more example embodiments of the present invention further relate to a method for driving a translatory movement of the retaining structure.

BACKGROUND

In particular, in the case of medical imaging devices used for medical imaging examinations during interventions, it may be necessary to adjust and retain a position of a component for the medical imaging examination depending on the examination situation relative to an examination area and/or relative to a gantry of the medical imaging device. This applies in particular when the gantry is mounted so as to be moveable relative to the examination area and/or when a person performing the intervention is in the immediate vicinity of the gantry while the gantry is being moved relative to the examination area for the medical imaging examination.

SUMMARY

An object of one or more embodiments of the present invention is to provide an alternative to conventional solutions involving retaining a component for a medical imaging examination of an examination area with respect to a gantry of a medical imaging device. Each subject matter of at least an independent claim achieves at least this object. The dependent claims take into account further advantageous aspects of embodiments of the present invention.

Independent of the grammatical term usage, individuals with male, female or other gender identities are included within the term.

An embodiment of the present invention relates to a system having a gantry of a medical imaging device, a retaining structure for retaining a component for a medical imaging examination of an examination area, a running gear and a guide apparatus,

- wherein the retaining structure is mounted so as to be moveable relative to the examination area via the guide apparatus, wherein the retaining structure has a first connection unit,
- wherein the gantry is mounted so as to be moveable relative to the examination area via the running gear, wherein the running gear is configured so as to drive a translatory movement of the gantry relative to the examination area,
- wherein the gantry has a second connection unit which is designed to correspond to the first connection unit, wherein it is possible via the first connection unit and the second connection unit to establish a connection which counteracts a change of position of the retaining structure relative to the gantry in such a manner that the retaining structure follows the translatory movement of the gantry relative to the examination area when the connection is established,
- wherein the retaining structure is mounted so as to be moveable relative to the gantry via the guide apparatus when the connection is released.

The translatory movement can be either rectilinear or curvilinear, for example. The translatory movement can be essentially horizontal, in particular horizontal, for example. The gantry can be mounted so as to be moveable relative to a base surface via the running gear, for example. The running gear can be configured so as to drive a translatory movement of the gantry relative to the base surface, for example. The base surface can be essentially horizontal, in particular horizontal, for example. In particular, it can be provided that the translatory movement of the gantry relative to the examination area is performed, in that the translatory movement of the gantry is performed relative to the base surface, while the examination area remains stationary relative to the base surface. The examination area can be an area of an examination object, for example. The examination object can be a patient, for example.

The connection can be releasable in particular in a non-destructive manner. The connection can be configured in particular so as to transmit a force from the gantry to the retaining structure, wherein the force drives a translatory movement of the retaining structure relative to the examination area in such a manner that the retaining structure follows the translatory movement of the gantry relative to the examination area. The force can be in particular a pulling force or a pushing force. In particular, the force can be sufficient in order to overcome any friction and/or restraint in the guide apparatus, so that the retaining structure can follow the translatory movement of the gantry relative to the examination area.

In particular, it can be provided that based on the friction and/or the restraint in the guide apparatus the retaining structure can be maintained in a position relative to the examination area and/or relative to the gantry via the guide apparatus while the connection is released. In particular, it can be provided that during the translatory movement of the gantry relative to the examination area, the retaining structure remains stationary relative to the examination area when the connection is released.

The translatory movement of the retaining structure relative to the examination area and the translatory movement of the gantry relative to the examination area can be in particular parallel to each other and have equal speed. In particular, the gantry can be mounted so as to be moveable relative to the examination area via the running gear in such a manner that the translatory movement of the gantry relative to the examination area can be performed. In particular, the retaining structure can be mounted so as to be moveable relative to the examination area via the guide apparatus in such a manner that the translatory movement of the retaining structure relative to the examination area can be performed. In particular, during the translatory movement of the retaining structure relative to the examination area, the retaining structure is mounted so as to be moveable relative to the examination area via the guide apparatus.

One embodiment provides that the connection counteracts, in particular counteracts in a non-positive locking manner, removal of the retaining structure from the gantry in such a manner that the retaining structure follows the translatory movement of the gantry relative to the examination area when the connection is established and the translatory movement of the gantry relative to the examination area is directed away from the retaining structure.

In particular, a system is disclosed here having a gantry of a medical imaging device, a retaining structure for retaining a component for a medical imaging examination of an examination area, a running rear and a guide apparatus,

- wherein the retaining structure is mounted so as to be moveable relative to the examination area via the guide apparatus, wherein the retaining structure has a first connection unit,
- wherein the gantry is mounted so as to be moveable relative to the examination area via the running gear, wherein the running gear is configured so as to drive a translatory movement of the gantry relative to the examination area,
- wherein the gantry has a second connection unit which is designed so as to correspond to the first connection unit, wherein via the first connection unit and the second connection unit a connection can be established which counteracts removal of the retaining structure from the gantry in such a manner that the retaining structure follows the translatory movement of the gantry relative to the examination area when the connection is established and the translatory movement of the gantry relative to the examination area is directed away from the retaining structure,
- wherein the retaining structure is mounted so as to be moveable relative to the gantry via the guide apparatus when the connection is released.

One embodiment provides that the connection is based on a magnetic attraction between the first connection unit and the second connection unit. In particular, it can be provided that the first connection unit has a magnet and that the second connection unit has a ferromagnetic material. Alternatively, it can be provided that the second connection unit has a magnet and that the first connection unit has a ferromagnetic material.

The magnet can be in particular a permanent magnet or an electromagnet. For example, the permanent magnet can be a rare earth magnet, in particular a neodymium magnet. The ferromagnetic material can be ferromagnetic steel, for example. The ferromagnetic material can be arranged in particular in a planar manner, for example in the form of a plate and/or a strip, in particular a sheet metal strip. For example, the magnet can have a planar outer surface against which the ferromagnetic material can lie in a planar manner.

One embodiment provides that the connection is released in a non-destructive manner when a positive-locking fit in the guide apparatus prevents the retaining structure from further following the translatory movement of the gantry relative to the examination area.

The positive-locking fit in the guide apparatus can arise, for example, from a mechanical range limitation and/or a tilting of parts of the guide apparatus relative to one another. In particular, when a ceiling arm of the guide apparatus should tilt or the gantry should move too far, the retaining structure can thus automatically detach itself from the gantry. This can prevent damage to people and/or equipment. Translatory movement of the gantry relative to the examination area can be directed in particular away from the retaining structure.

One embodiment provides that the system has a protective layer, wherein the protective layer is arranged on the first connection unit in such a manner that the protective layer protects a surface of the gantry, in particular a surface of the second connection unit, from an effect of scratches by the first connection unit, in particular while the connection is being established and/or in particular when the connection is established. For example, the protective layer can be made of a textile material, in particular felt. This can help to avoid scratches, particularly scratches to the paintwork, on the surface of the gantry.

One embodiment provides that the gantry has a casing that delimits an inner area of the gantry with respect to the surroundings of the gantry, wherein the second connection unit is attached to the casing. For example, the second connection unit can be arranged on a side of the casing that faces the inner area of the gantry and/or on a side of the casing that is facing the surroundings of the gantry. In particular, it can be provided that the retaining structure and/or the guide apparatus are located in the surroundings of the gantry.

In particular, it can be provided that the gantry has a pedestal for receiving the second connection unit, wherein the casing has a contact surface that faces the pedestal and has a curvature, wherein the pedestal has a first contact surface that follows the curvature of the contact surface of the casing and rests in a planar manner against the contact surface of the casing, wherein the second connection unit runs in a planar manner in a connection plane, wherein the pedestal has a second contact surface which is planar and is configured so as to receive the second connection unit. The second connection unit can be designed in particular in a planar manner, for example in the form of a plate and/or a strip, in particular a sheet metal strip.

In particular, positive-locking elements can be provided in the area of the first connection unit and/or in the area of the second connection unit and counteract a displacement of the first connection unit and the second connection unit relative to each other parallel to the connection plane in a form-locking manner when the connection is established. For example, the positive-locking elements can be recesses and/or shoulders as well as pins and/or frame elements corresponding to them.

One embodiment provides that the retaining structure has a retaining element for retaining the component and an articulation unit for the first connection unit, wherein the first connection unit is mounted via the articulation unit for the first connection unit so as to be pivotable relative to the retaining element about a pivot axis. This makes it possible, for example, to adjust an inclination of the first connection unit to match an inclination of the second connection unit without changing an inclination of the component. This can be particularly advantageous in the case of an oblique contact surface of the casing and a planar second connection unit resting directly on it, in which case the connection plane is then not vertical, for example. For example, the retaining element can be rod-shaped and/or aligned essentially vertically, in particular vertically.

In particular, it can be provided that the gantry has an opening and/or that the gantry is ring-shaped around a system axis of the gantry. For example, the opening can be tunnel-shaped and/or run along the system axis of the gantry. For example, the opening can run in a tunnel-shaped manner along the system axis of the gantry in such a manner that a supporting plate of a patient couch can be introduced into the tunnel-shaped opening along the system axis, in particular when a longitudinal direction of the supporting plate is essentially parallel to the system axis.

For example, the system axis can run through the opening, in particular through a central area of the opening. The system axis can pass through an isocenter of the medical imaging device, for example. In particular, it can be provided that the system axis is horizontal and/or that the translatory movement of the gantry relative to the examination area can occur parallel to the system axis.

The component can comprise a radiation protection apparatus to cover the opening, for example. In particular, it can be provided that the radiation protection apparatus prevents leakage of x-ray radiation from the opening when the connection is established. In particular, it can be provided that the radiation protection apparatus shields an area of the surroundings of the gantry from scattered beams of x-ray radiation that are essentially parallel to the system axis and/or that are directed coming from the opening onto the area of the surroundings of the gantry when the connection is established.

For example, the radiation protection apparatus can be located between the gantry and the area of the surroundings with respect to the system axis when the connection is established. For example, the area of the surroundings can be located in a section with respect to the system axis in which at least a part of the patient couch is located with respect to the system axis. In particular, the area of the surroundings can be above the patient table and/or in a horizontal direction perpendicular to the system axis adjacent to the patient table.

One embodiment provides that the component has a radiation protection plate and/or a display screen. For example, the component can run in a planar manner in a component plane. The component plane can be essentially vertical, in particular vertical, for example. For example, the component can be mounted via an articulation unit of the component so as to be pivotable relative to the retaining element about a vertical axis and/or about a horizontal axis.

For example, the radiation protection plate can be a lead glass plate and/or be configured so as to provide upper body radiation protection of a person. For example, the radiation protection plate can at least partially cover an opening in the gantry into which the examination area for the medical imaging examination can be introduced, in order to prevent leakage of x-ray radiation from the opening. For example, the display screen can be configured so as to display images of the examination area generated via the medical imaging device.

This allows the display screen and the radiation protection plate to move with the gantry without having to be permanently attached to the gantry. This allows the examination area, in which an intervention is taking place, for example, to be observed both directly from the outside and with the help of the images on the display screen by a person who is carrying out the intervention and is in the immediate vicinity of the gantry. If necessary, the retaining structure can be detached from the gantry and positioned relative to the examination area independently of the gantry via the guide apparatus.

In particular, it can be provided that the radiation protection plate prevents leakage of x-ray radiation from the opening when the connection is established. In particular, it can be provided that the radiation protection plate shields an area of the surroundings of the gantry from scattered beams of x-ray radiation that are essentially parallel to the system axis and/or that are directed coming from the opening onto the area of the surroundings of the gantry when the connection is established.

For example, the radiation protection plate can be located between the gantry and the area of the surroundings with respect to the system axis when the connection is established. For example, the area of the surroundings can be located in a section with respect to the system axis in which at least a part of the patient couch is located with respect to the system axis. In particular, the area of the surroundings can be above the patient couch and/or in a horizontal direction perpendicular to the system axis adjacent to the patient couch.

In particular, it can be provided that the radiation protection plate runs in a planar manner in a component plane and/or that the component plane is perpendicular to the system axis. For example, the radiation protection apparatus can have the radiation protection plate and/or a radiation protection curtain. The radiation protection curtain can be attached to the radiation protection plate and/or can hang down from the radiation protection plate, for example. The radiation protection curtain can be attached to the retaining structure and/or can hang down from the retaining structure, for example.

In particular, it can be provided that the system has the component and/or that the component is retained via the retaining structure. Furthermore, it can be provided that the component can be used for an intervention in the examination area. For example, the component can have a laser protection system and/or a medical intervention tool.

One embodiment provides that the guide apparatus has an articulated arm and/or a linear guide. In particular, it can be provided that the translatory movement of the retaining structure runs relative to the examination area and/or the translatory movement of the gantry relative to the examination area runs parallel to the linear guide.

One embodiment provides that the guide apparatus is attached to a ceiling of an examination room. For example, the linear guide can comprise a ceiling rail. The articulated arm can be designed as a ceiling arm, for example. In particular, it can be provided that a floor of the examination room supports the running gear.

One embodiment provides that the running gear is a rail-borne running gear and/or a wheeled running gear. In particular, the system can have rails on which the running gear runs. In particular, the rails can be integrated into the base surface. In particular, the running gear can have a set of wheels which roll on a base surface and/or on the rails.

One embodiment provides that the medical imaging device is a computed tomography device, a C-arm X-ray device or a magnetic resonance tomography device. In particular, the medical imaging device can be a rail-borne computed tomography device. In particular, it can be provided that the system has a medical imaging device and/or that the medical imaging device is configured so as to perform the medical imaging examination.

In particular, the medical imaging device can have a patient couch. The gantry can be mounted so as to be moveable relative to the patient couch via the running gear, for example. The running gear can be configured so as to drive a translatory movement of the gantry relative to the patient couch, for example. In particular, it can be provided that the translatory movement of the gantry is performed relative to the examination area, in that the translatory movement of the gantry is performed relative to the patient couch, while the examination area remains stationary relative to the patient couch and/or while the patient couch remains stationary relative to the base surface. The examination area can be an area of the patient couch, for example. When the patient couch is stationary relative to the base surface, the risk of cables and/or hoses, which are used for an intervention for example, becoming damaged is reduced in comparison to a patient couch which is moved relative to the base surface.

Moreover, an embodiment of the present invention relates to a method for driving a translatory movement of the retaining structure of the system relative to the examination area, the method comprising:

moving the retaining structure relative to the gantry in such a manner that the first connection unit and the second connection unit approach each other, establishing the connection via the first connection unit and the second connection unit, driving the translatory movement of the gantry relative to the examination area via the running gear, wherein via the connection a force is transmitted, in particular in a non-positive locking manner, from the gantry to the retaining structure, wherein the force drives the translatory movement of the retaining structure relative to the examination area in such a manner that the retaining structure follows the translatory movement of the gantry relative to the examination area.

One embodiment provides that the translatory movement of the gantry relative to the examination area is directed away from the retaining structure, wherein the retaining structure is pulled along by the running gear via the gantry and the connection.

One embodiment provides that the connection is released in a non-destructive manner in that a movement of the retaining structure and the gantry relative to each other is driven in such a manner that the first connection unit and the second connection move away from each other, in particular by overcoming an attraction force which acts between the first connection unit and the second connection unit.

The gantry of a medical imaging device typically has a supporting construction on which are arranged in particular components of the acquisition unit, for example the radiation source and/or the radiation detector. The supporting construction of the gantry has in particular such a high degree of rigidity and strength that the components of the acquisition unit are arranged on the supporting construction both relative to each other and also relative to the examination area in a geometry which is sufficiently defined for the medical imaging.

In the case of a computed tomography device, the gantry typically has a supporting frame and a rotor which is mounted so as to be able to rotate relative to the supporting frame, wherein the radiation source and the radiation detector are arranged on the rotor. Optionally, the gantry can have a tilting frame which is mounted so as to be able to tilt relative to the supporting frame, wherein the rotor is arranged on the tilting frame.

In the case of a C-arm X-ray machine, the gantry typically has a supporting frame and a C-arm which is mounted so as to be able to pivot relative to the supporting frame, wherein the radiation source and the radiation detector are arranged on the C-arm.

In the case of a magnetic resonance tomography device, the gantry typically has a supporting frame on which the main magnet and a first high-frequency antenna unit are arranged, the first high-frequency antenna unit being in the form of a body coil, also known to the person skilled in the art as a "body coil".

Within the scope of embodiments of the present invention, features which are described with respect to different embodiments of the present invention and/or different claim categories (method, use, device, system, arrangement etc.) can be combined to form further embodiments of the present invention. For example, a claim which relates to a device can also developed with features which are described or claimed in connection with a method and vice versa. Functional features of a method can be realized by physical components of embodiments of the present invention designed appropriately. The use of the indefinite articles "a" or "one" does not exclude the possibility that the features in question can also be present more than once.

BRIEF DESCRIPTION OF THE DRAWINGS

The present invention is described in detail below with the aid of exemplary embodiments with reference to the attached figures. The representation in the figures is schematic, greatly simplified and not necessarily true to scale.

FIG. 2 shows a view of a first connection unit and a second connection unit according to a further example.

DETAILED DESCRIPTION

Figure 1:
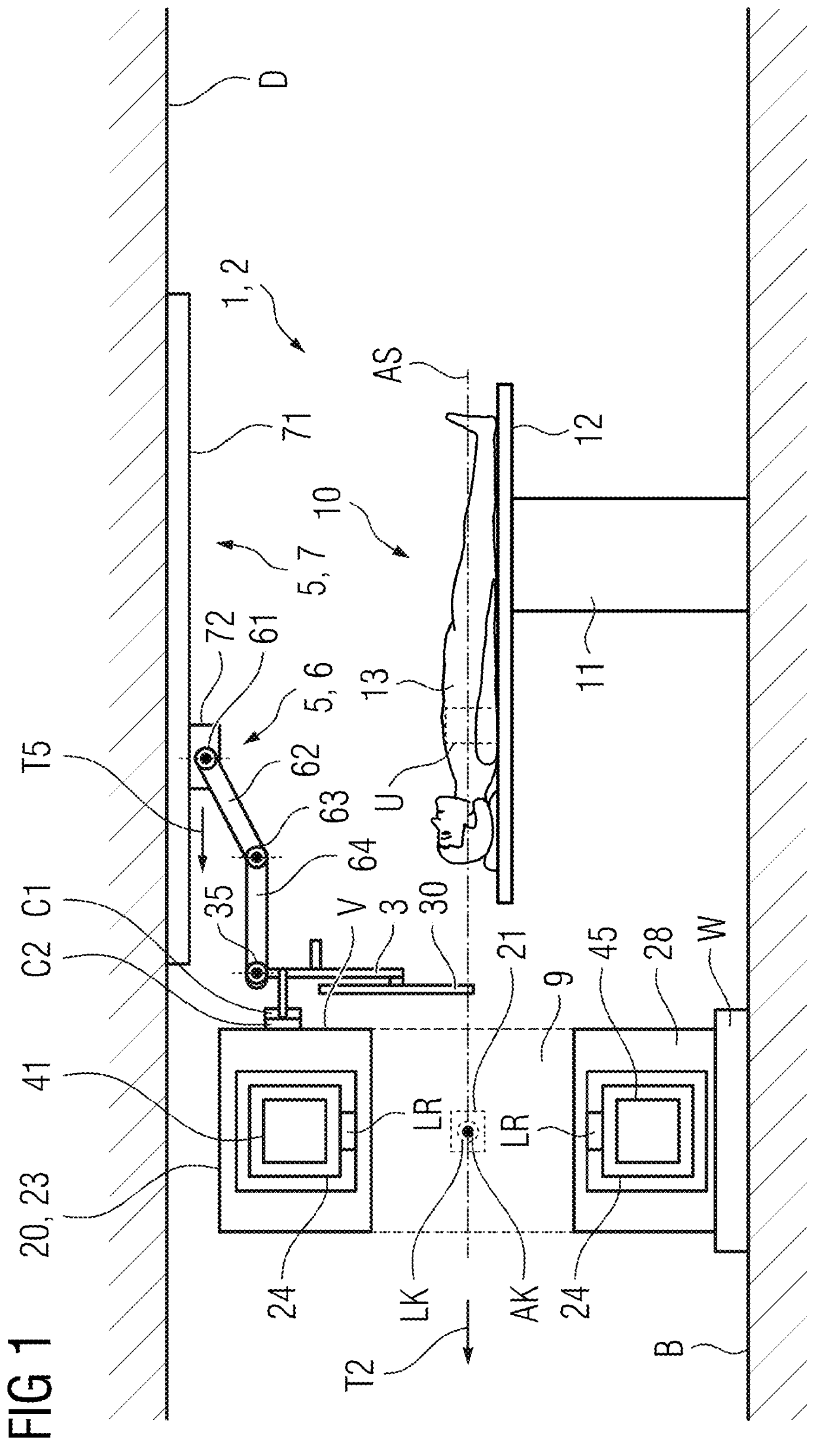
FIG. 1 shows a system having a gantry of a medical imaging device and a retaining structure for retaining a component.

FIG. 1 shows the system 1, having a gantry 20 of a medical imaging device 2, a retaining structure 3 for retaining a component 30 for a medical imaging examination of an examination area U, a running gear W and a guide apparatus 5, wherein the retaining structure 3 is mounted so as to be moveable relative to the examination area U via the guide apparatus 5, wherein the retaining structure 3 has a first connection unit C1, wherein the gantry 20 is mounted so as to be moveable relative to the examination area U via the running gear W, wherein the running gear W is configured so as to drive M3 a translatory movement of the gantry 20 relative to the examination area U, wherein the gantry 20 has a second connection unit C2 which is designed so as to correspond to the first connection unit C1, wherein it is possible via the first connection unit C1 and the second connection unit C2 to establish a connection which counteracts a change of position of the retaining structure 3 relative to the gantry 20 in such a manner that the retaining structure 3 follows the translatory movement of the gantry 20 relative to the examination area U when the connection is established, wherein the retaining structure 3 is mounted so as to be moveable relative to the gantry 20 via the guide apparatus 5 when the connection is released.

According to the example, it is provided that the connection counteracts removal of the retaining structure 3 from the gantry 20 in such a manner that the retaining structure 3 follows the translatory movement of the gantry 20 relative to the examination area U when the connection is established and the translatory movement of the gantry 20 relative to the examination area U is directed away from the retaining structure 3.

According to the example, it is provided that the connection is based on a magnetic attraction between the first connection unit C1 and the second connection unit C2. According to the example, it is provided that the connection is released in a non-destructive manner when a positive-locking fit in the guide apparatus 5 prevents the retaining structure 3 from further following the translatory movement of the gantry 20 relative to the examination area U.

According to the example, it is provided that the system 1 has a protective layer C0, wherein the protective layer C0 is arranged on the first connection unit C1 is such a manner that the protective layer C0 protects a surface of the gantry 20 from an effect of scratches by the first connection unit C1. According to the example, it is provided that the gantry 20 has a casing V that delimits an inner area 28 of the gantry 20 with respect to the surroundings of the gantry 20, wherein the second connection unit C2 is attached to the casing V.

The medical imaging device 2 has the gantry 20, the tunnel-shaped opening 9 and the patient couch 10. The gantry 20 has the rotor 24, the rotating bearing LR, the tilting bearing LK, the supporting frame 21 and the tilting frame 23. The tilting frame 23 is mounted on the supporting frame 21 via the tilting bearing LK so as to be able to tilt relative to the tilting frame 21 about the tilting axis AK. The tilting axis AK is perpendicular to the system axis AS. The rotor 24 is mounted on the tilting frame 23 via the rotating bearing LR so as to be able to rotate relative to the tilting frame 23 about a rotation axis AK. In the operating state of the system 1 shown in FIG. 1, the rotation axis is parallel to the system axis AS.

The patient 13 can be introduced into the tunnel-shaped opening 9. The acquisition area is located in the tunnel-shaped opening 9. It is possible to position the examination area U of the patient 13 in the acquisition area in such a manner that an X-ray beam can travel from the radiation source 41 to the examination area U and, after interacting with the examination area U, to the radiation detector 45. The patient couch 10 has the supporting pedestal 11 and the supporting plate 12 for supporting the patient 13. The supporting plate 12 can be introduced into the tunnel-shaped opening 9 via a translatory movement of the gantry 20 relative to the patient couch 10 in a longitudinal direction of the supporting plate 12, in particular along the system axis AS.

The medical imaging device 2 is designed so as to acquire acquisition data based on the electromagnetic radiation. The medical imaging device 2 has an acquisition unit. The acquisition unit is a projection data acquisition unit with the radiation source 41, for example an X-ray source, and the detector 45, for example an X-ray detector, in particular an energy-resolving X-ray detector. The rotor has the radiation source 41 and the radiation detector 45.

According to the example shown in FIG. 1, the second connection unit C2 is arranged on a side of the casing V that faces the surroundings of the gantry 20. For example, one dimension of the first connection unit C1 in a horizontal direction perpendicular to the system axis AS can be larger, in particular many times larger, than one dimension of the first connection unit C1 in a vertical direction, and/or smaller, in particular many times smaller, than one dimension of the opening 9 in the horizontal direction perpendicular to the system axis AS.

For example, one dimension of the second connection unit C2 in the horizontal direction perpendicular to the system axis AS can be larger, in particular many times larger, than one dimension of the second connection unit C2 in the vertical direction and/or smaller, in particular many times smaller, than a dimension of the opening 9 in the horizontal direction perpendicular to the system axis AS.

The component 30 is a radiation protection plate and runs in a planar manner in a component plane which is perpendicular to the system axis AS. The dimension of component 30 in the horizontal direction perpendicular to the system axis AS can be approximately equal to the dimension of the opening 9 in the horizontal direction perpendicular to the system axis AS. The opening 9 has an essentially circular cross-section. If the component 30 has a display screen, the display screen can run, for example, in a planar manner in a display screen component plane that is vertical and parallel to the system axis AS.

According to the example, it is provided that the guide apparatus 5 has an articulated arm 6 and a linear guide 7. According to the example, it is provided that the guide apparatus 5 is attached to a ceiling D of an examination room.

The linear guide 7 has the ceiling rail 71 and the rail carriage 72. The articulated arm 6 is attached to the rail carriage 72 and is mounted on the linear guide 7 so as to be moveable relative to the ceiling D and thus relative to the examination area U. The articulated arm 6 has the articulated units 61, 63 and 35, each of which allows pivoting about a corresponding vertical axis and pivoting about a corresponding horizontal axis. For example, the articulated arm section 64 can be pivoted relative to the articulated arm section 62 via the articulated unit 63 in each case independently of each other about a vertical axis and a horizontal axis. The vertical axis and the horizontal axis can also be skewed to with respect to each other, i.e. without a common point of intersection.

According to the example, it is provided that the running gear W is a rail-borne running gear and/or a wheeled running gear. According to the example, it is provided that the medical imaging device 2 is a computed tomography device.

Figure 2:
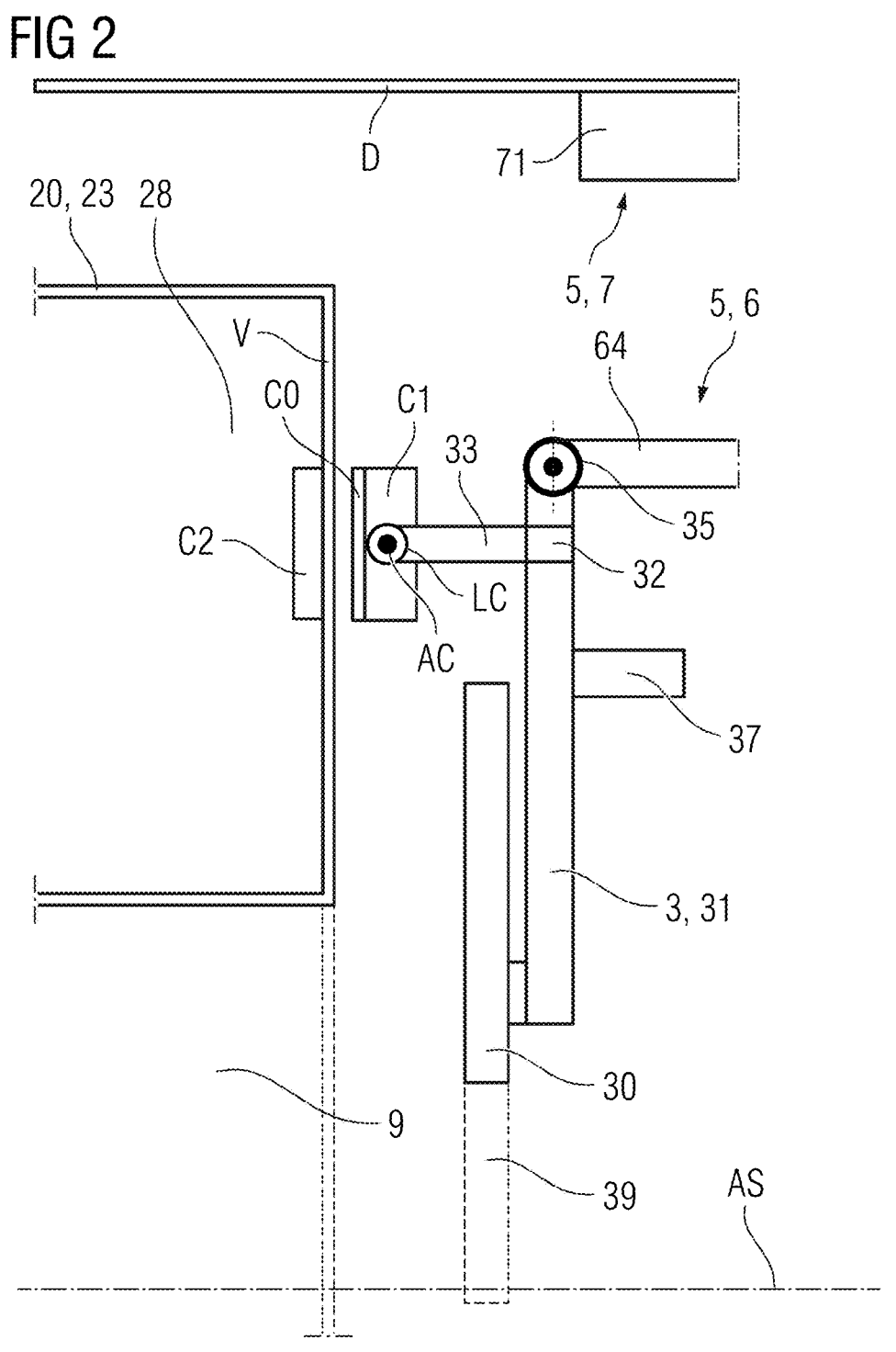

FIG. 2 shows a view of the first connection unit C1 and the second connection unit C2 according to a further example, wherein the second connection unit C2 is arranged on a side of the casing V facing the inner area 28 of the gantry 20.

In the operating state of the system 1 shown in FIG. 2, the connection is released so that during the translatory movement of the gantry 20 relative to the examination area U, the retaining structure 3 is stationary relative to the examination area U or can be moved independently of the gantry 20 relative to the examination area U via the guide apparatus 5.

According to the example, it is provided that the retaining structure 3 has a retaining element 31 for retaining the component 30 and an articulation unit LC for the first connection unit C1, wherein the first connection unit C1 is mounted via the articulation unit LC for the first connection unit C1 so as to be pivotable relative to the retaining element 31 about a pivot axis AC.

The retaining structure 3 has a clamp 33 and a screw 32 in order to connect the articulated unit LC to the retaining element 31 in particular to manually clamp them and screw them together. In this case, a height of the first connection unit C1 above the base surface B can be adjusted along the vertically oriented rod-shaped retaining element 31.

The radiation protection plate 30 has a recess 39. When the patient 13 is introduced into the opening 9, one edge of the recess 39 essentially adjoins the periphery of the patient 13, so that the radiation protection plate 30 essentially covers the gap that forms between the periphery of the patient 13 and one edge of the opening 9, preventing X-ray radiation from emerging from the opening 9.

In particular, it can be provided that the connection counteracts the change in position of the retaining structure 3 relative to the gantry 20 in such a manner that the first connection unit C1 follows a tilting movement of the tilting frame 23 relative to the supporting frame 21 via a pivoting movement about the pivot axis AC when the connection is established.

Figure 3:
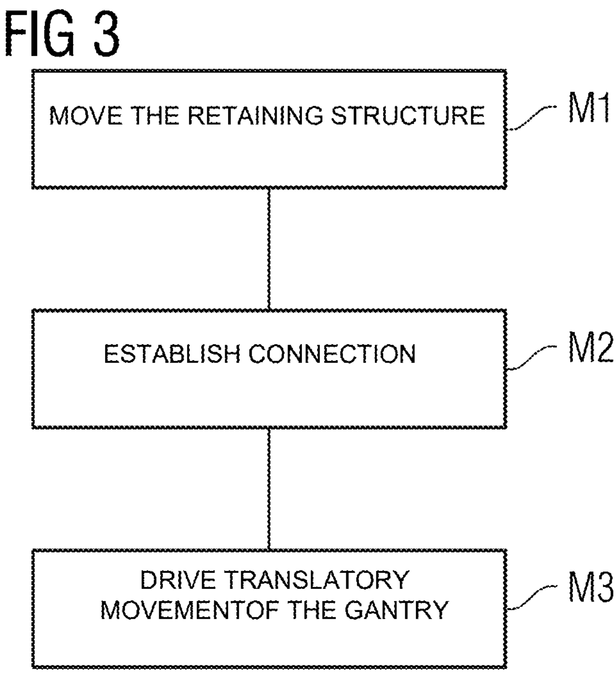
FIG. 3 shows a flow chart of a method for driving a translator movement of the retaining structure of the system.

FIG. 3 shows a flow chart of a method for driving a translatory movement of the retaining structure 3 of the system 1 according to one of claims 1 to 12 relative to the examination area U, the method comprising:

moving M1 the retaining structure 3 relative to the gantry 2 in such a manner that the first connection unit C1 and the second connection unit C2 approach each other, establishing M2 the connection via the first connection unit C1 and the second connection unit C2, driving M3 the translatory movement of the gantry 20 relative to the examination area U via the running gear W, wherein, via the connection, a force is transmitted from the gantry 20 to the retaining structure 3, wherein the force drives the translatory movement of the retaining structure 3 relative to the examination area U in such a manner that the retaining structure 3 follows the translatory movement of the gantry 20 relative to the examination area U.

For example, it is possible for the moving M1 of the retaining structure 3 relative to the gantry 20 to be driven in that a person applies a force by hand to the retaining structure 3 via the handle 37.

According to the example, it is provided that the translatory movement of the gantry 20 relative to the examination area U is directed away from the retaining structure 3, wherein the retaining structure 3 is pulled along by the running gear W via the gantry 20 and the connection.

The arrow T2 indicates the translatory movement of the gantry 20 relative to the examination area U. The arrow T2 indicates that the retaining structure 3 and at least parts of the guide apparatus 5 are pulled along by the running gear W via the gantry 20 and the connection.

According to the example, it is provided that the connection is released in a non-destructive manner in that a movement of the retaining structure 3 and the gantry 20 relative to each other is driven in such a manner that the first connection unit C1 and the second connection unit C2 move away from each other.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above-mentioned embodiments and/or to perform the method of any of the above-mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules.

Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A system comprising:

a gantry of a medical imaging device;

a retaining structure to retain a component for a medical imaging examination of an examination area, the retaining structure having a first connection unit;

a running gear;

a guide apparatus;

wherein the retaining structure is mounted to be moveable relative to the examination area via the guide apparatus, wherein the gantry is mounted to be moveable relative to the examination area via the running gear;

wherein the running gear is configured to drive a translatory movement of the gantry relative to the examination area;

wherein the gantry has a second connection unit that corresponds to the first connection unit;

wherein the first connection unit and the second connection unit are configured to establish a connection that counteracts a change in position of the retaining structure relative to the gantry such that the retaining structure follows the translatory movement of the gantry relative to the examination area when the connection is established; and wherein the retaining structure is mounted to be moveable relative to the gantry via the guide apparatus when the connection is released.

2. The system as claimed in claim 1, wherein the connection is configured to counteract removal of the retaining structure from the gantry such that the retaining structure follows the translatory movement of the gantry relative to the examination area when the connection is established and the translatory movement of the gantry relative to the examination area is directed away from the retaining structure.

3. The system as claimed in claim 1, wherein the connection is a magnetic connection between the first connection unit and the second connection unit.

4. The system as claimed in claim 1, wherein the connection is configured to be released in a non-destructive manner when a positive-locking fit in the guide apparatus prevents the retaining structure from further following the translatory movement of the gantry relative to the examination area.

5. The system as claimed in claim 1, further comprising:

a protective layer arranged on the first connection unit, the protective layer configured to protect a surface of the gantry from an effect of scratches by the first connection unit.

6. The system as claimed in claim 1, wherein the gantry includes a casing, the casing configured to delimit an inner area of the gantry with respect to surroundings of the gantry, and the second connection unit is attached to the casing.

7. The system as claimed in claim 1, wherein the retaining structure has a retaining element configured to retain the component, and an articulated unit for the first connection unit, and the first connection unit is mounted via the articulation unit, the first connection unit configured to pivot relative to the retaining element about a pivot axis.

8. The system as claimed in claim 1, wherein the component has at least one of a radiation protection plate or a display screen.

9. The system as claimed in claim 1, wherein the guide apparatus has at least one of an articulated arm or a linear guide.

10. The system as claimed in claim 1, wherein the guide apparatus is attached to a ceiling of an examination room.

11. The system as claimed in claim 1, wherein the running gear is at least one of a rail-borne running gear or a wheeled running gear.

12. The system as claimed in claim 1, wherein the medical imaging device is a computed tomography device, a C-arm X-ray device or a magnetic resonance tomography device.

13. A method for driving a translatory movement of the retaining structure of the system as claimed in claim 1 relative to the examination area, the method comprising:

moving the retaining structure relative to the gantry such that the first connection unit and the second connection unit approach each other;

establishing the connection via the first connection unit and the second connection unit; and driving the translatory movement of the gantry relative to the examination area via the running gear, wherein a force is transmitted from the gantry to the retaining structure via the connection, and the force drives the translatory movement of the retaining structure relative to the examination area such that the retaining structure follows the translatory movement of the gantry relative to the examination area.

14. The method as claimed in claim 13, wherein the translatory movement of the gantry relative to the examination area is directed away from the retaining structure, and the retaining structure is pulled along by the running gear via the gantry and the connection.

15. The method as claimed in claim 13, wherein the connection is configured to be released in a non-destructive manner in that a movement of the retaining structure and the gantry relative to each other is driven such that the first connection unit and the second connection unit move away from each other.

16. The system as claimed in claim 2, wherein the connection is configured to be released in a non-destructive manner when a positive-locking fit in the guide apparatus prevents the retaining structure from further following the translatory movement of the gantry relative to the examination area.

17. The system as claimed in claim 16, wherein the retaining structure has a retaining element configured to retain the component, and an articulated unit for the first connection unit, and the first connection unit is mounted via the articulation unit, the first connection unit configured to pivot relative to the retaining element about a pivot axis.

18. The system as claimed in claim 3, wherein the connection is configured to be released in a non-destructive manner when a positive-locking fit in the guide apparatus prevents the retaining structure from further following the translatory movement of the gantry relative to the examination area.

19. The system as claimed in claim 2, wherein the retaining structure has a retaining element configured to retain the component, and an articulated unit for the first connection unit, and the first connection unit is mounted via the articulation unit, the first connection unit configured to pivot relative to the retaining element about a pivot axis.

20. The system as claimed in claim 4, wherein the retaining structure has a retaining element configured to retain the component, and an articulated unit for the first connection unit, and the first connection unit is mounted via the articulation unit, the first connection unit configured to pivot relative to the retaining element about a pivot axis.

* * * * *